United States Patent
Odorzynski et al.

(10) Patent No.: US 6,245,050 B1
(45) Date of Patent: *Jun. 12, 2001

(54) DISPOSABLE ABSORBENT ARTICLE INCLUDING AN ELASTICIZED AREA

(75) Inventors: Thomas Walter Odorzynski, Green Bay; Joel Scott Sherman, Neenah, both of WI (US)

(73) Assignee: Kimberly-Clark Worldwide, Inc., Neenah, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/920,646

(22) Filed: Aug. 15, 1997

Related U.S. Application Data

(63) Continuation of application No. 08/555,011, filed on Nov. 9, 1995, now abandoned.

(51) Int. Cl.[7] .................................................. A61F 13/15
(52) U.S. Cl. .................... 604/385.16; 604/386; 604/387; 604/389; 604/390; 604/385.23
(58) Field of Search .................................... 604/386, 387, 604/389, 390, 385.16, 385.23

(56) References Cited

U.S. PATENT DOCUMENTS

| 4,024,312 | * | 5/1977 | Korpman .......................... 602/903 |
| 4,259,220 | | 3/1981 | Bunnelle et al. . |
| 4,418,123 | | 11/1983 | Bunnelle et al. . |

(List continued on next page.)

FOREIGN PATENT DOCUMENTS

| 2165486 | 6/1996 | (CA) . |
| 0 368 141 A3 | 5/1990 | (EP) . |
| 0 386 816 A3 | 9/1990 | (EP) . |
| 0 630 630 A2 | 12/1994 | (EP) . |
| WO 89/05334 A1 | 6/1989 | (WO) . |
| 95/01408 | 1/1995 | (WO) . |
| 95/05418 | 2/1995 | (WO) . |

OTHER PUBLICATIONS

ASTM Test Method D3236—1998, "Standard Test Method for Apparent Viscosity of Hot Melt Adhesives and Coating Materials," pp. 631–637.

PSTC Test Method PSTC-1 (Pressure Sensitive Tape Council)—"Peel Adhesion For Single Coated Pressure Sensitive Tapes At 180° Angle", pp. 23–24.

*Primary Examiner*—Dennis Ruhl
*Assistant Examiner*—Paul Shanoski
(74) *Attorney, Agent, or Firm*—Brian C. Pauls; Alyssa Dudkowski; Paul Yee

(57) ABSTRACT

Disclosed is a disposable absorbent article having a length and a width. The disposable absorbent article defines a first and second waist portion and a first and second longitudinal marginal portion. The disposable article includes the components of a backsheet layer, a topsheet layer, and an absorbent structure located between the topsheet layer and the backsheet layer. The article includes at least one elasticized area formed from an elastomeric, hot melt, pressure-sensitive adhesive, a first component and a second component, said first and second components being adhered to one another by said elastomeric, hot melt, pressure-sensitive adhesive. The elastomeric, hot melt, pressure-sensitive adhesive and the elasticized area formed therewith have the following characteristics: a) an adhesive bond strength sufficient to adhere said first and second components together during use of said disposable absorbent article; b) an elongation of at least 50 percent; c) a retractive force of less than 400 grams force per inch width at 90 percent elongation; d) a viscosity of less than 70,000 centipoise at 350° F.; and e) a cold flow value of less than 20 percent at 54° C.

33 Claims, 1 Drawing Sheet

U.S. PATENT DOCUMENTS

| | | | |
|---|---|---|---|
| 4,486,192 | 12/1984 | Sigl | 604/385 |
| 4,543,099 | 9/1985 | Bunnelle et al. | 604/385 A |
| 4,627,847 | 12/1986 | Puletti et al. | 604/366 |
| 4,692,161 | 9/1987 | Puletti et al. | 604/366 |
| 4,696,779 | 9/1987 | Wideman . | |
| 4,698,242 | 10/1987 | Salerno . | |
| 4,704,107 | 11/1987 | Coates | 604/357 |
| 4,718,898 | 1/1988 | Puletti et al. | 604/366 |
| 4,719,261 | 1/1988 | Bunnelle et al. . | |
| 4,761,198 | 8/1988 | Salerno . | |
| 4,798,603 | 1/1989 | Meyer et al. | 604/378 |
| 4,801,485 | 1/1989 | Sallee et al. . | |
| 4,998,928 | 3/1991 | Maletsky et al. | 604/365 |
| 5,032,120 | 7/1991 | Freeland et al. | 604/385.2 |
| 5,037,416 * | 8/1991 | Allen et al. | 604/385.2 |
| 5,100,398 | 3/1992 | Leroy et al. | 604/385.1 |
| 5,176,668 | 1/1993 | Bernardin | 604/368 |
| 5,176,672 | 1/1993 | Bruemmer et al. | 604/385.1 |
| 5,192,606 | 3/1993 | Proxmire et al. . | |
| 5,376,430 | 12/1994 | Swenson et al. . | |
| 5,415,644 | 5/1995 | Enloe | 604/385.2 |
| 5,509,915 | 4/1996 | Hanson et al. | 604/378 |

* cited by examiner

DISPOSABLE ABSORBENT ARTICLE INCLUDING AN ELASTICIZED AREA

This is a continuation of application Ser. No. 08/555,011, filed Nov. 9, 1995 now abandoned.

BACKGROUND OF THE INVENTION

The use of elastomeric materials to form elasticized areas in the design and construction of disposable absorbent articles is well known. Typically, such elasticized areas are formed by bonding elastomeric materials, such as natural or synthetic rubber, to the other components from which such disposable absorbent articles are formed. Generally, the elastomeric materials will be bonded to the absorbent article while the elastomeric materials are in a stretched condition. Upon relaxation, the elastomeric materials will operate to gather the components of the disposable absorbent articles to which they are attached. In this manner, elastomeric leg cuffs and waist gathers can be formed.

Attaching elastomeric materials to a disposable absorbent article while said elastomeric materials are in a stretched condition may be, from a manufacturing perspective, a difficult step to accomplish. Moreover, such elastomeric materials are typically attached to the disposable absorbent article through the use of adhesives such as hot melt adhesives. The presence of such adhesive has been found to reduce or eliminate the retractive forces exerted by such elastomeric material in the area in which the adhesives contact the elastomeric material and the disposable absorbent article to which they are attached.

SUMMARY OF THE INVENTION

In one aspect, the present invention is directed to a disposable absorbent article having a length and a width and defining first and second waist portions and first and second longitudinal marginal portions. The absorbent article comprises the following components: a backsheet layer, a topsheet layer, and an absorbent structure located between said topsheet layer and said backsheet layer. The disposable absorbent article further includes at least one elasticized area formed from an elastomeric, hot melt, pressure-sensitive adhesive, a first component and a second component, said first and second components being adhered to one another by said elastomeric, hot melt, pressure-sensitive adhesive. The elastomeric, hot melt, pressure-sensitive adhesive and the elasticized area formed therewith have the following properties:

A. an adhesive bond strength sufficient to adhere said first and second components together during use of said disposable absorbent article;

B. an elongation of at least 50 percent;

C. a retractive force of less than 400 grams force per (4.54 cm (1.0 inch) width at 90 percent elongation;

D. a viscosity of less than 70,000 centipoise at 176.7° F.; and

E. a cold flow value of less than 20 percent at 54° C.

DETAILED DESCRIPTION OF THE PREFERRED EMBODIMENTS

The present invention relates to a disposable absorbent article. The term "disposable absorbent article" is intended to refer to disposable articles intended to absorb discharged body fluids. Examples of disposable absorbent articles include diapers, adult incontinence products, training pants, feminine napkins, wound dressings, and the like. For ease of understanding, much of the following description will be made in terms of a disposable diaper. Nonetheless, it is to be understood that the present invention is equally suited for use on any disposable absorbent article.

Figure 1:
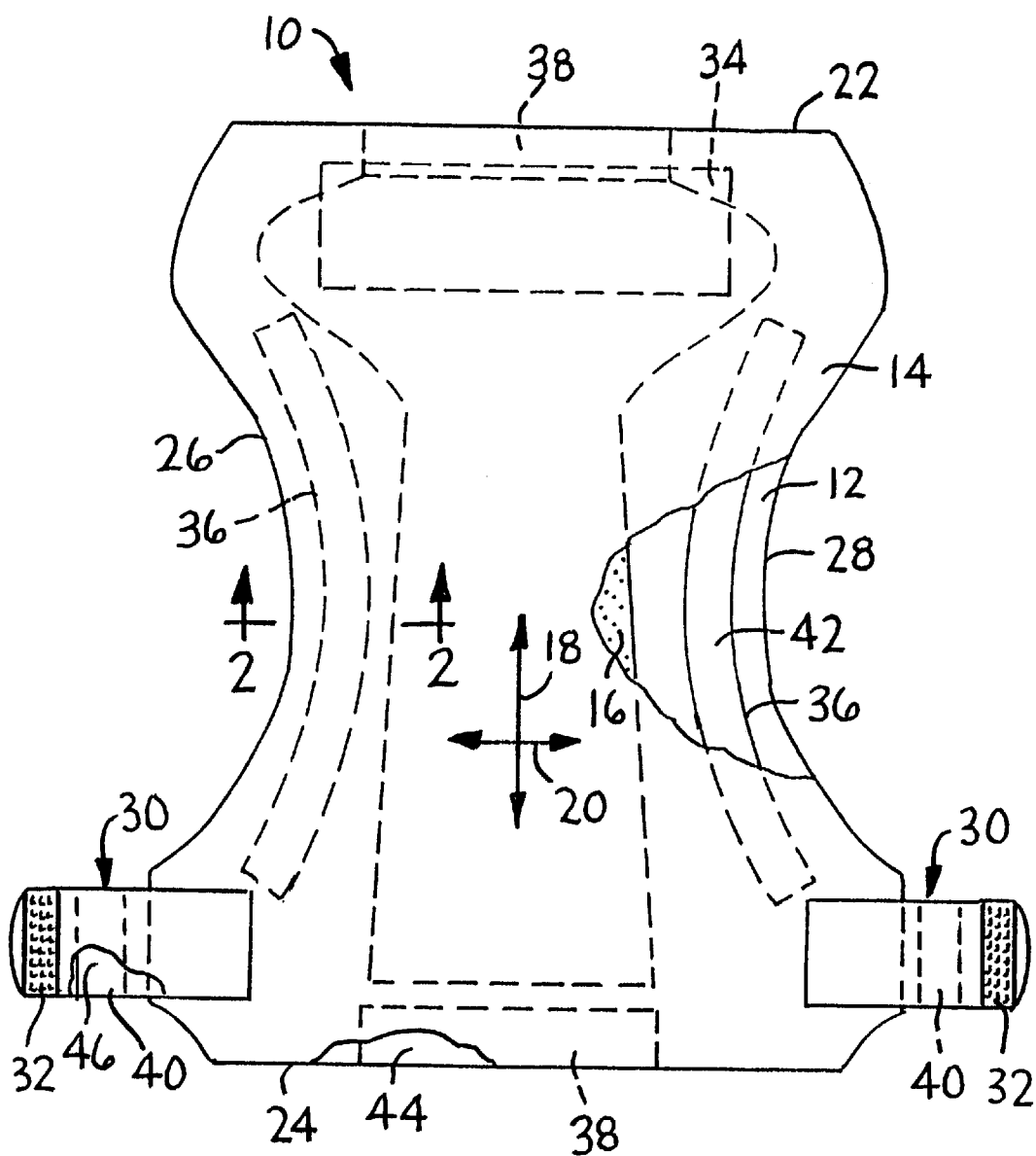
FIG. 1 illustrates a disposable absorbent article according to the present invention.

The disposable absorbent article of the present invention can best be understood by reference to FIG. 1 in which a disposable infant diaper 10 is illustrated. Disposable diaper 10 comprises the following components: a backsheet 12, a topsheet layer 14, and an absorbent structure 16 located between the backsheet layer 12 and the topsheet layer 14. The diaper 10 has a length in the direction of arrow 18 and a width in the direction of arrow 20. The diaper 10 further comprises a first waist portion 22 and a second waist portion 24. As used herein, the first and second waist portions are those portions of diaper 10 which are generally located at the waist of a wearer when the diaper is in place on the wearer's body. The diaper 10 further defines a first longitudinal marginal portion 26 and a second longitudinal marginal portion 28. The diaper 10 further includes mechanical fastening tabs 30 comprising hook material 32 and a loop material 34 adapted to releasably engage with the hook material 32.

The backsheet layer 12 may suitably comprise a material which is either liquid permeable or liquid impermeable. It is generally preferred that the backsheet layer 12 be formed from a material which is substantially impermeable to liquids. It is also desirable that the backsheet layer 12 be thin and flexible to improve consumer acceptance. For example, a typical backsheet layer can be manufactured from a thin plastic film or other flexible liquid-impermeable material. Examples of the material from which backsheet layer 12 may be formed include a polyethylene film having a thickness of from about 0.012 millimeter (0.5 mil) to about 0.051 millimeter (2.0 mils). If it is desired to present the backsheet layer 12 with a more clothlike feeling, the backsheet layer 12 may comprise a polyethylene film having a nonwoven web laminated to the outer surface thereof such as a spunbond web of polyolefin fibers. For example, a polyethylene film having a thickness of about 0.015 millimeter (0.6 mil) may have thermally laminated thereto a spunbond web of polyolefin fibers, which fibers have a thickness of about 1.5 to 2.5 denier per filament (dpf), which nonwoven web has a basis weight of about 24 grams per square meter (0.7 ounce per square yard). Methods of forming such clothlike backsheet layers are known to those skilled in the art.

Further, the backsheet layer 12 may be formed of a nonwoven or woven fibrous web layer which has been totally or partially constructed or treated to impart a desired level of liquid impermeability to selected regions that are adjacent to the absorbent structure 16. Still further, the backsheet layer 12 may optionally be composed of a microporous, "breathable" material which permits vapors to escape from the absorbent structure 16 while preventing liquid exudates from passing through the backsheet layer 12.

The topsheet layer 14 of the disposable diaper 10 suitably presents a body-facing surface which is compliant, soft feeling, and nonirritating to the wearer's skin. Further, the topsheet layer 14 may be less hydrophilic than the absorbent structure 16, to present a relatively dry surface to the wearer, and may be sufficiently porous to be liquid permeable, permitting liquid to readily penetrate through its thickness. A suitable topsheet layer 14 may be manufactured from a wide selection of web material such as porous foams, reticulated foams, apertured plastic films, natural fibers (for example, wood or cotton fibers), synthetic fibers (for example, polyester or polypropylene fibers), or a combination of natural or synthetic fibers. The topsheet layer 14 is suitably employed to help isolate the wearer's skin from liquids held in the absorbent structure 16.

Various woven and nonwoven fabrics can be used for the topsheet layer 14. For example, the topsheet layer may be composed of a meltblown or spunbond web of polyolefin fibers. The topsheet layer may also be a bonded-carded web composed of natural and/or synthetic fibers. The topsheet layer may be composed of a substantially hydrophobic material. The hydrophobic material may, optionally, be treated with a surfactant or otherwise processed to impart a desired level of wettability and hydrophilicity. In a particular embodiment of the present invention, the topsheet layer 14 comprises a nonwoven, spunbond, polypropylene fabric composed of about 2.8–3.2 denier per filament fibers formed into a web having a basis weight of about 22 grams per square meter and a density of about 0.06 gram per cubic centimeter. The fabric is surface treated with about 0.28 weight percent of surfactant commercially available from Rohm and Haas Company under the trade designation Triton X-102.

The absorbent structure 16 of the diaper 10 may suitably comprise a matrix of hydrophilic fibers, such as a web of cellulosic fluff, mixed with particles of a high-absorbency material commonly known as superabsorbent material. In a particular embodiment, the absorbent structure 16 comprises a mixture of superabsorbent hydrogel-forming particles and wood pulp fluff. The wood pulp fluff may be exchanged with a synthetic, polymeric, meltblown fiber or with a combination of meltblown fibers and natural fibers. The superabsorbent particles may be substantially homogeneously mixed with hydrophilic fibers or may be nonuniformly mixed. Alternatively, the absorbent structure 16 may comprise a laminate of fibrous webs and superabsorbent material or other suitable means of maintaining a superabsorbent material in a localized area.

The high-absorbency material can be selected from natural, synthetic and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble, but swellable. Such means can include, for example, physical entanglement, crystalline domains, covalent bonds, ionic complexes, ionic associations, hydrophilic associations such as hydrogen bonding, and hydrophobic associations or Van de Waal forces.

Examples of synthetic, polymeric, high-absorbency materials include the alkaline metal and ammonium salts of poly(acrylic acid) and poly(methacrylic acid), poly (acrylamides), poly(vinyl ethers), maleic anhydride copolymers with vinyl ethers and alpha-olefins, poly(vinyl pyrrolidone), poly(vinyl morpholinone), polylvinyl alcohol), and mixtures and copolymers thereof. Further polymers suitable for use in the absorbent structure include natural and modified natural polymers, such as hydrolyzed acrylonitrile-grafted starch, acrylic acid grafted starch, methylcellulose, carboxymethylcellulose, hydroxypropylcellulose, and the natural gums, such as alginates, xanthem gum, locust bean gum, and the like. Mixtures of natural and wholly or partially synthetic absorbent polymers can also be used in the present invention.

The high-absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. As a general rule, the high absorbency material is present in the absorbent structure in an amount of from about 5 to about 100 weight percent based on total weight of the absorbent structure 16.

Specific examples of disposable diapers suitable for use in the present invention, and other components suitable for use therein, are disclosed in the following U.S. patents and U.S. patent applications: U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al.; U.S. Pat. No. 5,415,644 issued May 16, 1995, to Enloe; and U.S. patent application Ser. No. 08/096,654 filed Jul. 22, 1993, in the name of Hanson et al., now U.S. Pat. No. 5,509,915 all of which are incorporated herein by reference. Other suitable components include, for example, containment flaps and waist flaps.

The disposable absorbent articles of the present invention include at least one elasticized area formed from an elastomeric, hot melt, pressure-sensitive adhesive, a first component, and a second component, the first and second components being adhered to one another by said elastomeric, hot melt, pressure-sensitive adhesive. The elastomeric, hot melt, pressure-sensitive adhesive and the elasticized area formed therewith have the following properties:

A. an adhesive bond strength sufficient to adhere said first and second components together during use of said disposable absorbent article;

B. an elongation of at least 50 percent;

C. a retractive force of less than 400 grams force per 2.54 cm(1.0 inch) width at 90 percent elongation;

D. a viscosity of less than 70,000 centipoise at 176.7° C.(350° F.) and

E. a cold flow value of less than 20 percent at 54° C.

As used herein, reference to an adhesive bond strength refers to the strength of the bond adhering said first and second components together. The adhesive bond strength can be quantified by the amount of force required to separate the first and second components from one another according to the test method set forth below in connection with the examples. The elastomeric, hot melt, pressure-sensitive adhesive of the present invention suitably has an adhesive bond strength, as determined by the test method set forth below in connection with the examples, of at least 100 grams force per inch (2.54 cm) width, suitably of at least 200 grams force per inch (2.54 cm) width, alternatively of at least 400 grams force per inch (2.54 cm) width, alternatively of at least from about 200 grams force per inch (2.54 cm) width to about 700 grams force per inch width.

As used herein, reference to the elongation of the elasticized area formed with the elastomeric, hot melt, pressure-sensitive adhesive refers to the elongation of the elasticized area and is suitably determined as set forth below in connection with the examples. The elasticized area formed with the elastomeric, hot melt, pressure-sensitive adhesive suitably has an elongation Of at least 50 percent, alternatively of at least 150 percent, alternatively of from about 50 percent to about 200 percent.

As used herein, reference to the retractive force of the elasticized area formed with the elastomeric, hot melt, pressure-sensitive adhesive refers to the retractive force exhibited by the elasticized area one minute after stretching to 90% of the elongation of the elasticized area, and is suitably determined as set forth below in connection with the examples. The elasticized area suitably has a retractive force of less than about 400 grams force per inch (2.54 cm) width, alternatively of less than about 275 grams force per inch (2.54 cm) width, alternatively of from about 100 grams force per inch (2.54 cm) width to about 250 grams force per inch (2.54 cm) width.

As used herein, reference to the viscosity of the elastomeric, hot melt, pressure-sensitive adhesive refers to the viscosity, in centipoise at 176° C.(350° F.) as determined by a Brookfield Model DV-lll Programmable Rheometer (spindle size of 27) commercially available from E. Johnson Engineering & Sales Co., Elm Hurst, Ill. 60126. A suitable test method is set forth in American Society for Testing and Materials (ASTM) test method D-3236. The elastomeric, hot melt, pressure-sensitive adhesives of the present invention suitably have a viscosity of less than 70,000 centipoise at 176° C.(350° F.), alternatively of less than 50,000, alternatively of from about 20,000 to about 35,000.

Reference to the cold flow value of the elasticized area formed with the elastomeric, hot melt, pressure-sensitive adhesive refers to the amount of elastic composite growth after the elasticized area has been exposed to a temperature of 54° C. for a period of 24 hours. The cold flow value of the elasticized areas are suitably determined as set forth below in connection with the examples. The elasticized area formed with the elastomeric, hot melt, pressure-sensitive adhesives of the present invention suitably have a cold flow value of less than about 20 percent, alternatively of less than 15 percent, alternatively of from about 5 percent to about 10 percent.

A number of elastomeric components are known for use in the design and manufacture of disposable absorbent articles. For example, disposable absorbent articles are known to contain elasticized leg cuffs, elasticized waist portions, and elasticized fastening tabs. Thus, with reference to FIG. 1, the elasticized areas of the disposable absorbent articles according to the present Invention may form elasticized leg cuffs 36, waist elastics 38, and elasticized fastening tabs 40. That is, the elastomeric, hot melt, pressure-sensitive adhesives described above may be applied to components of a disposable diaper to form the elasticized areas 42, 44 and 46 indicated as defining elasticized leg cuff 36, waist elastics 38 and elasticized fastening tabs 40, respectively.

The disposable absorbent articles of the present invention need only comprise one elasticized area formed from an elastomeric, hot melt, pressure-sensitive adhesive described above. The elasticized areas are suitably formed by applying the hot melt, pressure-sensitive adhesive described above to one or more components of the disposable absorbent article. For example, the elasticized hot melt, pressure-sensitive adhesives may be applied to the backsheet 12, the topsheet 14, the absorbent structure 16 or a separate component such as a carrier sheet, containment flap, waist flap, or the like, which first component is then brought into contact with and adhered to a second component of the diaper. The second component may be a separate component or may be a different portion of the first component. For example, the elastomeric, hot melt, pressure-sensitive adhesive may be applied to the backsheet 12 which is then adhered to the topsheet 14 to form an elasticized area which functions as a leg or waist elastic. Alternatively, the elastomeric, hot melt, pressure-sensitive adhesive may be applied to one or both sides of a thin carrier sheet which is then sandwiched between the backsheet and topsheet to form an elasticized area.

If the elastomeric, hot melt, pressure-sensitive adhesive is applied directly, or via a carrier sheet, to one or more components of a disposable absorbent article without first being stretched, the component(s) to which it is applied will need to be capable of being stretched in a least one direction in order to produce an elasticized area. For example, the component could be necked, or gathered, in order to allow it to be stretched after application of the elastomeric, hot melt, pressure-sensitive adhesive. Various post treatments, such as treatment with grooved rolls, which alter the mechanical properties of the garment component, are also suitable for use.

The elastomeric, hot melt, pressure-sensitive adhesives are suitably applied to one or more components of the disposable absorbent article by spraying, film forming, slot coating, and the like. By carefully selecting the viscosity of the elastomeric, hot melt, pressure-sensitive adhesives, the adhesives can be applied with conventional adhesive application systems, such as spray nozzles, slot coating, and the like.

Alternatively, the elastomeric, hot melt, pressure-sensitive adhesive may be applied to a chill roll or similar device, in the form of a strand or ribbon. The strand or ribbon is then stretched and thinned, and applied to the first component and second component to form an elasticized area.

After being applied to the disposable absorbent article, the elastomeric, hot melt, pressure-sensitive adhesive suitably contracts to gather the components of the disposable absorbent article to which it is attached. The elastomeric, hot melt, pressure-sensitive adhesives are capable not only of introducing a degree of elasticity to the disposable absorbent article, but are also capable of providing a construction adhesive function. That is, the adhesives adhere together the components of the disposable absorbent article to which they are in contact. Thus, in one embodiment, it is preferred that the elasticized area formed from the elastomeric, hot melt, pressure-sensitive adhesive described above be free of other adhesive materials, preferably of both other adhesive materials and other elastomeric materials. It is also possible that the elastomeric, hot melt, pressure-sensitive adhesives do not constrict upon cooling but, instead, tend to retract to approximately its original dimension after being elongated during use of the product. This, of course, necessitates that the component of the disposable absorbent article to which such an elastomeric, hot melt, pressure-sensitive adhesive Is attached be capable of being elongated in at least one direction.

The elasticized areas are suitably formed by applying the elastomeric, hot melt, pressure-sensitive adhesives to the disposable absorbent article in the form of a film. The film suitably has a thickness of about 0.001 inch to about 0.05 inch, alternatively of from about 0.001 to about 0.01 (about 2.54 mm to about 2.54 mm), and a width of from about 0.05 inch, to about 3.0 inches (about 1.27 mm to about 7.62 mm), alternatively of from about 0.5 inch to about 1.5 inches (about 1.27 cm to about 3.81 cm). When the elastomeric, hot melt, pressure-sensitive adhesive is in the form of a film, the film can impart barrier properties to the elasticized area formed therewith.

Suitable elastomeric, hot melt, pressure-sensitive adhesives comprise elastomeric polymers, tackifying resins, plasticizers, oils and antioxidants. Such elastomeric, hot melt, pressure-sensitive adhesives are available from Findley Adhesives, Inc., Wauwatosa, Wis., under the trade designation Findley H2503 and H2504.

Figure 2:
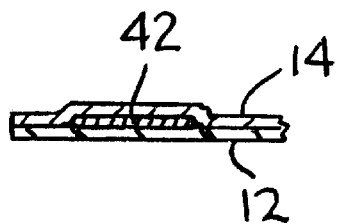
FIG. 2 is a cross-sectional view taken along line 2—2 of FIG. 1.

FIG. 2 illustrates a cross-sectional view taken along line 2—2 of FIG. 1.

Test Methods

Adhesive Bond Strength

The adhesive bond strength of an elasticized area according to the present invention is determined as follows. A test sample of the elasticized area is cut from the absorbent product. The elasticized area preferably has the dimensions of 2.0 inches wide by 4.0 inches long (5.08 cm by 10.16 cm). If the elasticized area is not this large, the largest sample possible (but less than 2.0"×4") is used for testing. It Is not necessary for the sample to be tested to have an elastomeric, hot melt, pressure-sensitive adhesive located continuously across the length and/or width of the sample. Thus, for example, if the elastomeric, hot melt, pressure-sensitive adhesive is applied between the first and second components in a spray pattern, line pattern, or other intermittent application, a test sample having the stated length and width can be cut from the product so as to encompass that area of the elasticized area having generally the greatest coverage of the elastomeric, hot melt, pressure-sensitive adhesive across its width and length. The adhesive bond strength is determined through the use of a tensile tester such as a SINTECH tensile tester commercially available from the Sintech Co., Carry, N.C., Model No. II. A 90° peel adhesion test is run in order to determine the grams of force needed to pull apart the first and second components of the elasticized area. Such a test method is generally described in Pressure Sensitive Tape Counsel Test Method 1. Specifically, 1.25 inches (3.175 cm) or more of the 4 inch length of the test sample has the first and second components peeled apart. The first component is then clamped in the upper Jaw of the tensile tester, and the second component is clamped in the lower Jaw of the tensile tester. The tensile tester is set to the following conditions:

Crosshead Speed:

300 millimeters per minute
Full-scale load:

5,000 grams
Start measurements:

10 millimeters
Gauge Length:

(Jaw spacings) 1.0 inch (2.54 cm)

The Instron tensile tester is then engaged. The test is terminated after approximately 100 millimeters on a 2"×4" sample. Twenty data points per second are collected for a total of about 400 data points. The average of these data points is reported as the adhesive bond strength. The results from the tensile tester are normalized to a sample having a width of 1 inch. At least three test samples are subjected to the above testing with the results being averaged and normalized to produce the reported adhesive bond strength.

Elongation

The elongation of an elasticized area according to the present invention is suitably determined as follows. A 1" wide by 4" long elasticized area is provided. The central 3 inch (7.62 cm) area of the sample is marked. The test sample is then stretched to its maximum length, and the distance between the marks is measured and recorded as the "stretched to stop length." The percent elongation is determined according to the following formula:

$$\frac{\text{stretched to stop length (in inches)} - 3}{3} \times 100$$

If a 1"×4" elasticized area is not available, the largest sample possible (but less than 1"×4") is used for testing with the test method being adjusted accordingly.

Retractive Force

The retractive force of an elasticized area according to the present invention is determined on a test sample having a width of 1 inch and a length of 3 inches. A test apparatus having a fixed clamp and an adjustable clamp is provided. The adjustable clamp is equipped with a strain gauge commercially available from S. A. Mieier Co. under the trade designation Chatillon DFIS2 digital force gauge. The test apparatus can elongate the test sample to a given length. One longitudinal end of the test sample is clamped in the fixed clamp of the test apparatus with the opposite longitudinal end being clamped in the adjustable clamp fitted with the strain gauge. The test sample is elongated to 90 percent of its elongation (as determined by the test method set forth above). The retractive force is read from the digital force gauge after I minute. At least three samples of the elasticized area are tested in this manner with the results being averaged and reported as grams force per inch width.

Cold Flow

The cold flow properties of the elasticized area according to the present invention is determined on a test sample having a width of 1 inch and a length of 3 inches. The test sample is placed in an aging room at a temperature of 54° C. for 24 hours. At the end of that time, the test sample is removed from the aging room and the length of the test sample is measured and recorded as the "aged length." The percent cold flow is determined by the following formula: [(Aged length—original length)/original length]×100.

EXAMPLES

Example 1

An elastomeric, hot melt, pressure-sensitive adhesive available from Findley Adhesives under the trade designation of H-2504 was processed through a Nordson hot melt glue system (available from the Nordson Corporation) at a temperature of 350° F. The material was passed through a slot die having a width of 6 inches and a thickness of 8 mils. The elastomeric, hot melt, pressure-sensitive adhesive was then placed on a chill roll having a temperature of 56–57° F. traveling at a speed of 6 feet per minute. The elastomeric, hot melt, pressure-sensitive adhesive was then stretched to approximately 575–600% of its length and was brought into contact with two webs of material. The first web of material was a 0.5 ounce per square yard, 2 denier per filament polypropylene spunbond material, thermally bonded to a 0.4 mil (0.3 ounce per square yard) cast film. The second web of material was a pointbonded carded web of 2–2.5 denier per filament side by side polyethylene/polypropylene bicomponent fibers having a basis weight of 0.7 ounce per square yard. Both web materials had a width greater than the quenched elastomeric, hot melt, pressure-sensitive adhesive. The quenched elastomeric, hot melt, pressure-sensitive adhesive was placed between the two web materials and run through a compression roll having a nip pressure of 100 pounds per square inch. The elastomeric, hot melt pressure-sensitive adhesive was bonded to the film side of the first web. The finished laminate was allowed to retract and was collected. The finished laminate had the following properties; an adhesive bond strength of 655.2 grams per one inch width; an elongation of 150%; a 125 gram retractive force and a cold-flow value of 0%.

Example 2

An elastomeric, hot melt, pressure-sensitive adhesive available from Findley Adhesives under the trade designation H-2504 was processed through a Nordson hot melt glue system at a temperature of 350° F. The material was passed through a slot die having a width of 6 inches and a thickness of 8 mils. The elastomeric, hot melt, pressure-sensitive adhesive was then placed on a chill roll having a temperature of 56–57° F. traveling at a speed of 6 feet per minute. The elastomeric, hot melt, pressure-sensitive adhesive was then stretched approximately 575–600% of its length and was brought into contact with two pointbonded, bonded carded webs of 2–2.5 denier per filament side-by-side polyethylene/polypropylene bicomponent fiber webs having a basis weight of 0.7 ounce per square yard. The quenched elastomeric, hot melt, pressure-sensitive adhesive was located between the two web materials and run through a compression roll having a nip pressure of 100 pounds per square inch. The finished laminate was allowed to retract and was collected. The finished laminate had the following properties; an adhesive bond strength of 457.8 grams per one inch width; an elongation of 160%; a 133 gram retractive force; and a cold-flow value of 8.3%.

Example 3

An elastomeric, hot melt, pressure-sensitive adhesive available from Findley Adhesives under the trade designation of H-2303 was processed through a Nordson hot melt glue system at a temperature of 375° F. The material was passed through a slot die having a width of 6 inches and a thickness of approximately 3 mils. The elastomeric, hot melt, pressure-sensitive adhesive was then placed on a chill roll having a temperature of 56–57° F. traveling at a speed of approximately 20 feet per minute. The elastomeric, hot melt, pressure-sensitive adhesive was then stretched 575% of its length and was brought into contact with two webs of polypropylene spunbond material having a basis weight of 0.7 ounce per square yard and being formed from 3 denier per filament fibers. Both spunbond materials have a width greater than the quenched elastomeric, hot melt, pressure-sensitive adhesive. The quenched elastomeric, hot melt, pressure-sensitive adhesive was placed between the two spunbond layers and passed through a compression nip roll having a nip pressure of 100 pounds per square inch. The finished laminate was allowed to retract and was collected. The finished laminate had the following properties; an adhesive bond strength of 612 grams per one inch width; an elongation of 105%; a 116 gram retractive force; and a cold-flow value of 8.3%.

Comparative Example 4

An elastomeric, hot melt, pressure-sensitive adhesive available from Findley Adhesives under the trade designation of H-2209 was processed through a hot melt glue system at 325–350° F. The material was passed through a slot die having a width of 1.50 inch and a thickness of approximately 10 mils and placed on a strip of differential release liner material commercially available from Akrosil Inc. A piece of the H-2209 material 1.50 inches wide by 1.0 inch long was removed from the release liner material, elongated 1200 percent, and was placed between two layers of 3 denier per filament, 0.7 ounce per square yard polypropylene spunbond material, and was nipped at a pressure of 90 pounds per square inch. The finished laminate was allowed to retract and was collected. The finished laminate had the following properties; an adhesive bond strength of 162 grams per inch width; an elongation of 125%; a 174 gram retractive force; and a cold-flow value of 50 to 100%.

While the present invention has been described in terms of the specific embodiments set forth herein, those skilled in the art will recognize numerous variations and alterations thereof which are intended to be within the scope of the claims appended hereto.

What is claimed:

1. A disposable absorbent article having a length and a width defining first and second waist portions and first and second longitudinal marginal portions, said article comprising the following components:
    a backsheet layer;
    a topsheet layer; and
    an absorbent structure located between said topsheet layer and said backsheet layer, said article including at least one elasticized area formed from an elastomeric, hot melt, pressure-sensitive adhesive, a first component and a second component, said first and second components being adhered to one another by said elastomeric, hot melt pressure-sensitive adhesive, said elastomeric, hot melt pressure-sensitive adhesive and the elasticized area formed therewith being elongateable in a first direction, said elasticized area having an original length in the first direction, said elasticized area being retractable after elongation to a length substantially equivalent to said original length, the elasticized area having the following properties:
    a) an adhesive bond strength sufficient to adhere said first and second components together during use of said disposable absorbent article;
    b) an elongation of at least 50 percent;
    c) a retractive force of less than 400 grams force per inch width at 90 percent elongation;
    d) a viscosity of less than 70,000 centipoise at 350° F.; and
    e) a cold flow value of less than 20 percent at 54° C.

2. The disposable absorbent article according to claim 1 wherein said elastomeric, hot melt, pressure-sensitive adhesive has an adhesive bond strength of at least 100 grams force per inch width.

3. The disposable absorbent article according to claim 1 wherein said elastomeric, hot melt, pressure-sensitive adhesive has an adhesive bond strength of at least 400 grams force per inch width.

4. The disposable absorbent article according to claim 1 wherein said elasticized area has an elongation of at least 150 percent.

5. The disposable absorbent article according to claim 1 wherein said elasticized area has an elongation of from 50 percent to 200 percent.

6. The disposable absorbent article according to claim 1 wherein said elasticized area has a retractive force of less than 275 grams force per inch width.

7. The disposable absorbent article according to claim 1 wherein said elasticized area has a retractive force of from about 100 grams force per inch width to about 250 grams force per inch width.

8. The disposable absorbent article according to claim 1 wherein said elasticized area has a cold flow value of less than 15 percent at 54° C.

9. The disposable absorbent article according to claim 1 wherein said elastomeric, hot melt, pressure-sensitive adhesive is in the form of a film.

10. The disposable absorbent article according to claim 9 wherein said film has a thickness of from about 0.001 inch to about 0.05 inch, and a width of from about 0.05 inch to about 3.0 inches.

11. The disposable absorbent article according to claim 10 wherein said film has a thickness of about 0.001 inch to about 0.01 inch and a width of from about 0.5 inch to about 1.5 inches.

12. The disposable absorbent article according to claim 1 wherein said elasticized area is present in said first and second longitudinal marginal portions.

13. The disposable absorbent article according to claim 10 wherein said elasticized area is present in said first and second longitudinal marginal portions.

14. The disposable absorbent article according to claim 1 wherein said elasticized area is present in said first and second waist portions.

15. The disposable absorbent article according to claim 10 wherein said elasticized area is present in said first and second waist portions.

16. The disposable absorbent article according to claim 1 further comprising a containment flap.

17. The disposable absorbent article according to claim 16 wherein said containment flap includes said elasticized area.

18. The disposable absorbent article according to claim 17 wherein said first component is said containment flap, and said second component is a different portion of said containment flap.

19. A disposable absorbent article having a length and a width defining first and second waist portions and first and second longitudinal marginal portions, said article comprising the following components:
   a backsheet layer;
   a topsheet layer; and
   an absorbent structure located between said topsheet layer and said backsheet layer, said article including at least one elasticized area formed from an elastomeric, hot melt, pressure-sensitive adhesive, a first component and a second component, said first and second components being adhered to one another by said elastomeric, hot melt, pressure-sensitive adhesive, said elastomeric, hot melt, pressure-sensitive adhesive and the elasticized area formed therewith being elongateable in a first directions said elasticized area having an original length in the first direction, said elasticized area being retractable after elongation to a length substantially equivalent to said original length, the elasticized area having the following properties:
   a) an adhesive bond strength of at least 100 grams force per inch width;
   b) an elongation of at least 150 percent;
   c) a retractive force of less than 275 grams force per inch width at 90 percent elongation;
   d) a viscosity of less than 50,000 centipoise at 350° F.; and
   e) a cold flow value of less than 15 percent at 54° C.

20. The disposable absorbent article according to claim 12 wherein said first component is formed by a portion of said topsheet layer and said second component is formed by a portion of said backsheet layer.

21. The disposable absorbent article according to claim 13 wherein said first component is formed by a portion of said topsheet layer and said second component is formed by a portion of said backsheet layer.

22. The disposable absorbent article according to claim 14 wherein said first component is formed by a portion of said topsheet layer and said second component is formed by a portion of said backsheet layer.

23. The disposable absorbent article according to claim 15 wherein said first component is formed by a portion of said topsheet layer and said second component is formed by a portion of said backsheet layer.

24. A disposable absorbent article having a length and a width defining first and second waist portions and first and second longitudinal marginal portions, said article comprising:
   a backsheet layer;
   a topsheet layer;
   an absorbent structure located between said topsheet layer and said backsheet layer; and
   at least one elasticized area comprising an elastomeric adhesive adhering a first component to a second component, said elasticized area being capable of elongation in a first direction, said elasticized area having a non-elongated original length in said first direction, said elasticized area being retractable after elongation to a length substantially equivalent to said original length.

25. The disposable absorbent article of claim 24 wherein said first component is formed by a portion of said topsheet layer and said second component is formed by a portion of said backsheet layer.

26. The disposable absorbent article of claim 25 wherein said elastomeric adhesive forms a film-like layer whereby said elasticized area forms a barrier.

27. The disposable absorbent article of claim 24 wherein one said second component comprises a fastening tab.

28. The disposable absorbent article of claim 24 wherein adhesives present in said elasticized area consist of said elastomeric adhesive and wherein elastic elements present in said elasticized area consist of said elastomeric adhesive.

29. A disposable absorbent article having a length and a width defining first and second waist portions and first and second longitudinal marginal portions, said article comprising:
   a backsheet layer;
   a topsheet layer;
   an absorbent structure located between said topsheet layer and said backsheet layer; and
   at least one elasticized area comprising an astomeric adhesive adhering a portion of said backsheet layer to a portion of said topsheet layer, said elasticized area being capable of elongation in a first direction, said elasticized area having a non-elongated original length in said first direction, said elasticized area being retractable after elongation to a length substantially equivalent to said original length an said elasticized area having a cold flow value of less than 20 percent at 54° C.

30. The disposable absorbent article of claim 29 wherein said elasticized area is disposed adjacent a leg opening in said article.

31. The disposable absorbent article of claim 29 wherein said elasticized area is disposed in one of the first and second waist portions.

32. The disposable absorbent article of claim 29 wherein adhesives present in said elasticized area consist of said elastomeric adhesive and wherein elastic elements present in said elasticized area consist of said elastomeric adhesive.

33. The disposable absorbent article of claim 29 wherein said elastomeric adhesive forms a film-like layer whereby said elasticized area forms a barrier.

* * * * *

UNITED STATES PATENT AND TRADEMARK OFFICE
CERTIFICATE OF CORRECTION

PATENT NO. : 6,245,050 B1
DATED : June 12, 2001
INVENTOR(S) : Thomas Walter Odorzynski et al.

It is certified that error appears in the above-identified patent and that said Letters Patent is Title page,
Item [56], References Cited, U.S. PATENT DOCUMENTS,
Delete "4,024,312", and substitute -- 4,021,312 --.

Column 1,
Line 52, delete "(4.54", and substitute -- 2.54 --.
Line 54, delete "F;", and substitute -- C; --.
Line 55, delete "and", and substitute -- (350°F) --.

Column 5,
Lines 12 and 20, delete "176°", and substitute -- 176.7° --.

Column 6,
Line 47, delete "Is", and substitute -- is --.
Line 53, after the word "inch", insert -- (.0254mm to about 1.27mm) --.
Lines 54 and 55, delete "(about 2.54 mm to about 2.54 mm).
Line 56, after "7.62", delete "mm", and substitute -- cm --.

Column 7,
Line 13, delete "Is", and substitute -- is --.

Column 9,
Line 33, delete "H-2303", and substitute -- H-2503 --.

UNITED STATES PATENT AND TRADEMARK OFFICE
CERTIFICATE OF CORRECTION

PATENT NO. : 6,245,050 B1
DATED : June 12, 2001
INVENTOR(S) : Thomas Walter Odorzynski et al.

It is certified that error appears in the above-identified patent and that said Letters Patent is <u>Column 12,</u>
Line 43, delete "astomeric", and substitute with -- elastomeric --.
Line 50, delete "an", and substitute with -- and --.

Signed and Sealed this

Twenty-fifth Day of December, 2001

Attest:

Attesting Officer

JAMES E. ROGAN
*Director of the United States Patent and Trademark Office*